(12) United States Patent
Vortman et al.

(10) Patent No.: US 9,981,148 B2
(45) Date of Patent: May 29, 2018

(54) ADAPTIVE ACTIVE COOLING DURING FOCUSED ULTRASOUND TREATMENT

(75) Inventors: Kobi Vortman, Haifa (IL); Shuki Vitek, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 907 days.

(21) Appl. No.: 12/910,622

(22) Filed: Oct. 22, 2010

(65) Prior Publication Data
US 2012/0101412 A1 Apr. 26, 2012

(51) Int. Cl.
| | |
|---|---|
| *A61N 7/00* | (2006.01) |
| *A61N 7/02* | (2006.01) |
| *A61B 90/00* | (2016.01) |
| *A61B 17/00* | (2006.01) |
| *A61B 18/00* | (2006.01) |

(52) U.S. Cl.
CPC .............. *A61N 7/02* (2013.01); *A61B 90/04* (2016.02); *A61B 90/37* (2016.02); *A61B 2017/00084* (2013.01); *A61B 2018/00023* (2013.01); *A61B 2090/0472* (2016.02); *A61B 2090/374* (2016.02); *A61N 7/022* (2013.01)

(58) Field of Classification Search
CPC ........... A61B 5/01; A61B 90/37; A61B 90/04; A61N 7/02; A61N 7/022
USPC ......................................................... 601/3
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,074,564 A | 2/1978 | Anderson |
| 4,206,653 A | 6/1980 | Lemay |
| 4,339,952 A | 7/1982 | Foster |
| 4,441,486 A | 4/1984 | Pounds |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,586,512 A | 5/1986 | Do-huu et al. |

(Continued)

FOREIGN PATENT DOCUMENTS

| | | |
|---|---|---|
| CN | 1257414 A | 6/2000 |
| DE | 4345308 | 2/2001 |

(Continued)

OTHER PUBLICATIONS

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

(Continued)

*Primary Examiner* — Joseph M Santos Rodriguez
(74) *Attorney, Agent, or Firm* — Morgan, Lewis & Bockius LLP

(57) ABSTRACT

Disclosed are thermal treatment methods that involve monitoring and/or actively adjusting the temperature of targeted and/or non-targeted tissues.

5 Claims, 5 Drawing Sheets

(56) References Cited

U.S. PATENT DOCUMENTS

| | | |
|---|---|---|
| 4,636,964 A | 1/1987 | Jacobs et al. |
| 4,662,222 A | 5/1987 | Johnson |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,304 A | 7/1995 | Oppelt et al. |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,501,655 A | 3/1996 | Rolt et al. |
| 5,507,790 A | 4/1996 | Weiss |
| 5,520,188 A | 5/1996 | Hennige et al. |
| 5,526,814 A | 6/1996 | Cline et al. |
| 5,526,815 A | 6/1996 | Granz et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,810,008 A | 9/1998 | Dekel et al. |
| 5,817,036 A | 10/1998 | Anthony et al. |
| 5,823,962 A | 10/1998 | Schaetzle et al. |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,558 A | 9/2000 | Rosenschein et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,554,826 B1 | 4/2003 | Deardorff |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,823,216 B1 | 11/2004 | Salomir et al. |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,211,055 B2 | 5/2007 | Diederich et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,510,536 B2 | 3/2009 | Foley et al. |
| 7,511,501 B2 | 3/2009 | Wexler |

(56) References Cited

U.S. PATENT DOCUMENTS

| | | | |
|---|---|---|---|
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| RE43,901 E | 1/2013 | Freundlich et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2002/0188229 A1 | 12/2002 | Ryaby |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0147919 A1 | 7/2004 | Behl et al. |
| 2004/0210134 A1 | 10/2004 | Hynynen et al. |
| 2004/0236253 A1 | 11/2004 | Vortman et al. |
| 2004/0267126 A1 | 12/2004 | Takeuchi |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0203444 A1 | 9/2005 | Schonenberger et al. |
| 2005/0240126 A1 | 10/2005 | Foley et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058671 A1 | 3/2006 | Vitek et al. |
| 2006/0058678 A1 | 3/2006 | Vitek et al. |
| 2006/0106300 A1 | 5/2006 | Seppenwoolde et al. |
| 2006/0173385 A1 | 8/2006 | Lidgren et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0083383 A1 | 4/2007 | Van Bael et al. |
| 2007/0098232 A1 | 5/2007 | Matula et al. |
| 2007/0167781 A1 | 7/2007 | Vortman et al. |
| 2007/0197918 A1 | 8/2007 | Vitek et al. |
| 2007/0219470 A1 | 9/2007 | Talish et al. |
| 2008/0027342 A1 | 1/2008 | Rouw et al. |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0108900 A1 | 5/2008 | Lee et al. |
| 2008/0183077 A1 | 7/2008 | Moreau-Gobard et al. |
| 2008/0228081 A1 | 9/2008 | Becker et al. |
| 2008/0312562 A1 | 12/2008 | Routh et al. |
| 2009/0088623 A1 | 4/2009 | Vortman et al. |
| 2009/0096450 A1 | 4/2009 | Roland |
| 2010/0056962 A1 | 3/2010 | Vortman et al. |
| 2010/0106063 A1* | 4/2010 | Chomas et al. ............. 601/3 |
| 2012/0035464 A1 | 2/2012 | Raju et al. |
| 2012/0191020 A1 | 7/2012 | Vitek et al. |

FOREIGN PATENT DOCUMENTS

| | | |
|---|---|---|
| DE | 10102317 A1 | 8/2002 |
| EP | 31614 A1 | 7/1981 |
| EP | 558029 A3 | 9/1994 |
| EP | 875203 A2 | 11/1998 |
| EP | 1132054 | 9/2001 |
| EP | 1582886 A1 | 10/2005 |
| EP | 151073 | 11/2005 |
| EP | 1774920 | 4/2007 |
| EP | 1790384 | 5/2007 |
| EP | 2629850 A1 | 8/2013 |
| FR | 2806611 A1 | 8/2002 |
| JP | 5-300910 A | 11/1993 |
| JP | 11313833 | 11/1999 |
| JP | 2002-505596 A | 2/2002 |
| WO | WO-91/00059 | 1/1991 |
| WO | WO-98/52465 | 11/1998 |
| WO | WO-00/31614 | 6/2000 |
| WO | 2001/043640 A2 | 6/2001 |
| WO | WO-01/058337 | 8/2001 |
| WO | WO-01/66189 | 9/2001 |
| WO | WO-02/58791 | 9/2001 |
| WO | WO-01/80709 | 11/2001 |
| WO | 2002/043804 A1 | 6/2002 |
| WO | WO-03/013654 | 2/2003 |
| WO | 2003/070105 A1 | 8/2003 |
| WO | WO-03/097162 | 11/2003 |
| WO | WO-03/098232 | 11/2003 |
| WO | WO-04/093686 | 11/2004 |
| WO | WO-05/58029 | 6/2005 |
| WO | WO-06/018837 | 2/2006 |
| WO | WO-06/025001 | 3/2006 |
| WO | WO-06/072958 | 7/2006 |
| WO | WO-06/087649 | 8/2006 |
| WO | WO-06/119572 | 11/2006 |
| WO | WO-07/047247 | 4/2007 |
| WO | WO-07/073551 | 6/2007 |
| WO | 2007/093998 A1 | 8/2007 |
| WO | WO-08/039449 | 4/2008 |
| WO | WO-08050278 | 5/2008 |
| WO | WO-08/75203 | 6/2008 |
| WO | WO-08/119054 | 10/2008 |
| WO | WO-09/055587 | 4/2009 |
| WO | WO-09/094554 | 7/2009 |
| WO | WO-09/124301 | 10/2009 |
| WO | WO-10/082135 | 7/2010 |
| WO | 2012/052847 A1 | 4/2012 |

OTHER PUBLICATIONS

International Search Report and Written Opinion dated Mar. 14, 2012 for International Application No. PCT/IB2011/002866 (12 pages).

Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

Jolesz et al., "Integration of interventional MRI with computer-assisted surgery," J. Magnetic Resonance Imaging. 12:69-77 (2001).

Kohler et al., "Volumetric HIFU Ablation guided by multiplane MRI thermometry," 8th Intl. Symp. on Therapeutic Ultrasound, edited by E.S. Ebbini, U. of Minn. (Sep. 2009).

(56) References Cited

OTHER PUBLICATIONS

Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Mougenot et al., "MR monitoring of the near-field HIFU heating," 8th Intl. Symp. on Therapeutic Ultrasound, edited by E.S. Ebbini, U. of Minn. (Sep. 2009).
Vykhodtseva et al., "MRI detection of the thermal effects of focused ultrasound on the brain," Ultrasound in Med. & Biol., vol. 26, No. 5, pp. 871-880 (2000).
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
FDA Approves Exablate 2000 as Non-invasive surgery for Fibroids, Oct. 22, 2004.
Chen et al., "MR Acoustic Radiation Force Imaging: Comparison of Encoding Gradients." Proc. Intl. Soc. Mag. Reson. Med. 16 (May 3-9, 2008).
Herbert et al., "Energy-based adaptive focusing of waves: application to ultrasonic transcranial therapy," 8th Intl. Symp. on Therapeutic Ultrasound (Sep. 10-13, 2009).
Medel et al., "Sonothrombolysis: An emerging modality for the management of stroke," Neurosurgery, vol. 65, No. 5, pp. 979-993. (Oct. 22, 2009).
Vimeux et al., "Real-time control of focused ultrasound heating based on rapid MR thermometry," Investig. Radiology, vol. 43, No. 3, pp. 190-193. (Feb. 15, 2008).
Office Action dated Jun. 19, 2013 for EP Patent Application No. 11805586.2 (2 pages).
"MR Guided Focused Ultrasound; Non-Invasive Surgery for Uterine Fibroids", ExAblate 2000, InSightec, Ltd., 2000, 2 pages.
Examination Report in Chinese Patent Application No. 01819665.9, dated Mar. 24, 2006, 9 pages (5 pages of English Translation and 4 pages of Official Copy).
Notice of Allowance and Issuance in Chinese Patent Application No. 01819665.9, dated Jan. 10, 2007, 4 pages.
Examination Report in Japanese Patent Application No. 2002-545773, dated Apr. 20, 2007, 5 pages (3 pages of English Translation and 2 pages of Office Action).
Examination Report in European Patent Application No. 01998377.4, dated Apr. 19, 2007, 2 pages.
Examination Report in European Patent Application No. 01998377.4, dated Jun. 29, 2006, 3 pages.
Examination Report in European Patent Application No. 01998377.4, dated Nov. 21, 2005, 2 page.
Examination Report in European Patent Application No. 01998377.4, dated Jan. 23, 2007, 3 pages.
PCT International Application No. PCT/IB2003/005551, International Written Opinion dated Sep. 10, 2004.
PCT International Application No. PCT/IB2004/001498, International Search Report and Written Opinion dated Aug. 31, 2004, 8 pages.
PCT International Application No. PCT/IB2004/001512, International Preliminary Report on Patentability dated Nov. 25, 2005, 5 pages.
PCT International Application No. PCT/IB2005/002273, International Search Report and Written Opinion dated Dec. 20, 2005, 6 pages.
PCT International Application No. PCT/IB2005/002413, International Search Report and Written Opinion dated Nov. 22, 2005, 8 pages.
PCT International Application No. PCT/IB2006/001641, International Search Report and Written Opinion dated Sep. 25, 2006, 8 pages.
PCT International Application No. PCT/IB2006/003300, International Search Report and Written Opinion dated Feb. 14, 2008, 7 pages.
PCT International Application No. PCT/IB2007/001079, International Search Report and Written Opinion dated Dec. 10, 2007, 11 pages.
PCT International Application No. PCT/IB2007/002134, International Search Report and Written Opinion dated Dec. 13, 2007, 8 pages.
PCT International Application No. PCT/IB2007/002140, International Search Report and Written Opinion dated Dec. 29, 2008, 7 pages.
PCT International Application No. PCT/IB2008/003069, International Search Report and Written Opinion dated Apr. 27, 2009, 10 pages.
PCT International Application No. PCT/IB2011/002866, International Preliminary Report on Patentability dated May 2, 2013, 8 pages.
PCT International Application No. PCT/IL2001/000340, International Written Opinion dated Feb. 24, 2003.
PCT International Application No. PCT/IL2001/001084, International Preliminary Examination Report, dated Mar. 17, 2003, 6 pages.
PCT International Application No. PCT/IL2001/001084, International Search Report and Written Opinion dated Mar. 26, 2002, 7 pages.
PCT International Application No. PCT/IL2001/001084, Reply to Written Opinion dated Nov. 28, 2002, 7 pages.
PCT International Application PCT/IL2002/000477, International Written Opinion dated Feb. 25, 2003, 9 pages.
Hynynen et al., "Principles of MR-Guided Focused Ultrasound", Chapter 25, pp. 237-243.
Levy et al., "Least Squares Conformal Maps for Automatic Texture Atlas Generation", Proceedings of the 29th Annual Conference on Computer Graphics and Interactive Techniques, Jul. 2002, 10 pages.
McDannold et al., "Quality Assurance and System Stability of a Clinical MRI-Guided Focused Ultrasound System: Four-Year Experience", Medical Physics, vol. 33, No. 11, Nov. 2006, pp. 4307-4313.
Umemura et al., "The Sector-Vortex Phased Array: Acoustic Field Synthesis for Hyperthermia", IEEE Transactions on Ultrasonics, Ferroelectrics and Frequency Control, vol. 36, No. 2, Mar. 1989, pp. 249-257.
U.S. Appl. No. 13/013,449, filed Jan. 25, 2011, Vitek et al.; Final Office Action dated Aug. 13, 2014: Advisory Action dated Sep. 17, 2014; and Non-Final Office Action dated Dec. 29, 2014.

\* cited by examiner

ADAPTIVE ACTIVE COOLING DURING FOCUSED ULTRASOUND TREATMENT

FIELD OF THE INVENTION

The present invention relates, generally, to ultrasound treatment of body tissues and, more specifically, to systems and methods for cooling non-target tissues during focused ultrasound therapy.

BACKGROUND

Body tissues, such as tumors, can be destroyed by heat. One way to apply thermal energy to internal body tissue is to focus high-intensity ultrasound waves into the tissue, using a phased array of piezoelectric transducer elements. Such treatment can reduce or even eliminate the need for invasive surgery to remove the tissue. For effective treatment, it is important that a sufficient thermal dose be reached during each ultrasound application (or "sonication") to ablate, coagulate, or otherwise destroy the portion of the target tissue being heated. Moreover, it is important to avoid painful or damaging heat build-up in healthy tissues surrounding the target tissue. Heating of these surrounding tissues results from the absorption of ultrasound energy outside the focus region, e.g., the absorption of ultrasound by tissue located along the ultrasound beam path between the transducer and the target, or the absorption of ultrasound transmitted through the target by tissues behind the target. Further, heating of the surrounding tissues can result from thermal conduction between the target tissue and nearby healthy tissues.

Non-target tissues can often be protected by allowing cooling periods between successive sonications. Such cooling periods, however, tend to significantly prolong the total treatment time, which can be substantial if numerous sonications are required to fully destroy the target tissue. Since treatment requires conscious sedation and lying inside a magnetic resonance imaging (MRI) apparatus, shortening treatment time is highly desired. To eliminate or reduce the need for cooling periods, non-target tissues can sometimes be actively cooled. For example, during the treatment of superficial tumors, active cooling may be applied to the skin, allowing for faster (i.e., more energy-intensive) treatment of the tumor without overheating the skin. Similarly, other tissue interfaces, such as the rectal wall or endometrium, may be cooled. The resulting temperature gradient between the tumor and the tissue interface achieves the desired protection of non-target tissue. In conventional active cooling, the cooled tissue is typically maintained at a fixed temperature substantially below an estimated threshold temperature for thermal damage, providing a margin of safety.

Depending on the particular anatomy of the region to be treated, active cooling can itself have practical limitations because it can counteract the necessary heating of the tumor; that is, the tumor may experience cooling from a nearby cooled interface, e.g., through direct contact or through blood vessels that go through the interface. As a consequence, a higher ultrasound intensity is required to thermally destroy the tumor. The increased ultrasound intensity, in turn, may expose surrounding tissues that are not amenable to cooling (e.g., due to their location deep inside the body) to thermal damage. Thus, setting the level of cooling involves a trade-off between protecting cooled non-target tissues and limiting the risk to non-target tissue that cannot be cooled. Accordingly, there is a need for improved ultrasound therapy and cooling protocols that provide adequate protection for all non-target tissues while supplying a therapeutically effective dose of thermal energy to the target tissue.

SUMMARY

The present invention is generally directed to focused ultrasound therapy, or other thermal treatment modalities, that involve the heating of target tissue and the active cooling of non-target tissue, at least during a portion of the treatment. Various embodiments provide techniques that may be employed, individually or in combination, to avoid both insufficient cooling (which would permit damage to the cooled tissue) and excessive levels of cooling (which would result in damage to uncooled non-target tissues). In general, cooling protocols in accordance with the invention may involve variable cooling levels that are adjusted to the specific anatomy, target tissue location, acoustic beam path, acoustic energy density profile, and/or thermal properties of the target and surrounding tissues (including, for example, the thermal response of the tissues to heat sources or sinks during treatment, acoustic absorption, and blood perfusion). To facilitate the determination of adequate cooling levels, some embodiments include monitoring the temperature of a body region that encompasses the target tissue as well as the surrounding healthy tissues that may be affected by the ultrasound treatment. The term "monitoring," as used herein, denotes determining the temperature as it evolves in time, which may be accomplished by direct or indirect measurements of the temperature (e.g., using temperature sensors or imaging apparatus that provide image data indicative of the temperature) or, alternatively, by computations of the temperature based on known heat sources and/or sinks and the thermal properties of the tissues. The temperature computations may involve estimates, as long as the accuracy of the estimates is within limits that allow clinically meaningful (and safe) adjustments of the cooling levels.

In some embodiments, the treatment and cooling protocols exploit different thermal responses (including, e.g., different thermal time constants) between the target tissue and a nearby non-target tissue, or between different non-target tissues. For example, if a tissue interface located between the transducer and a tumor to be treated has a faster thermal time constant than the tumor (i.e., it cools down faster in response to cooling the interface), cooling and tumor treatment may be cycled. Each cycle begins with a cooling period that quickly reduces the temperature of the tissue interface, but does not immediately affect the temperature of the tumor (at least not significantly). Then, the tumor is sonicated while cooling of the tissue interface continues. Following the sonication, active cooling of the tissue interface is interrupted, or the interface is even heated, to avoid the undesired incidental cooling of the tumor.

For large tumors or multiple tumors located in the same organ, different time constants may also be exploited by varying the focus location during a transient cooling period. Assume, for example, that two tumors in the prostate are to be treated, one tumor lying close to the rectal wall and one close to the anterior prostate capsule. The rectal wall is amenable to cooling, whereas the anterior prostate capsule is much less amenable. Cooling applied to the rectal wall will ultimately also lower the temperature of the prostate. As a result, the temperature of the muscle adjacent the anterior capsule can rise above that of the prostate during tumor sonication, making the muscle susceptible to thermal damage. Such damage may be avoided if the tumor close to the muscle is treated at the beginning of the cooling period, while the prostate temperature is in a transient state and the temperature difference between the prostate and the muscle is below a certain threshold. Once this threshold is exceeded, the ultrasound focus may be shifted to the second tumor near the rectal wall, which is sufficiently distant from the muscle to avoid damage to it. This results in time-efficient treatment while minimizing thermal damage of non-target tissue. Changes in the location of the ultrasound focus may also occur periodically, and optionally in combination with temporal cycling of cooling and heating periods as described above.

In a first aspect, the invention provides a thermal treatment method that includes heating a target tissue, monitoring a temperature field in a region encompassing both the target tissue and a non-target tissue, and actively adjusting the temperature of the non-target tissue based on the temperature field. The target may be heated, for example, by focusing ultrasound into the target tissue, and ultrasound focusing parameters (e.g., the location of intensity of the ultrasound focus) may be adjusted based on the monitored temperature field. In some embodiments, the ultrasound focus location is cycled between different targets at different distances from the non-target tissue. The different targets may have different thermal time constants. The temperature field may be monitored using MRI thermometry (also referred to as thermal MRI) or another thermal imaging technique. Alternatively or additionally, the time evolution of the temperature field may be determined computationally, e.g., based on calibrated parameters, which may relate tissue thermal response to a thermal stimulus applied to the tissue. The temperature of the non-target tissue may be adjusted by actively cooling and, in some embodiments, thereafter actively heating the non-target tissue. Active cooling or heating (i.e., active temperature adjustments) may be accomplished by flowing a fluid through a heat exchanger in contact with the non-target tissue, and changing, for example, the flow rate or temperature of the fluid. Heating of the target tissue and active cooling of the non-target tissue may be repeated in cycles. In some embodiments, the target tissue and the non-target tissue have different thermal time constants, and the step of actively adjusting the temperature of the non-target tissue is based at least in part on the difference between the thermal time constants.

In another aspect, an ultrasound treatment method for treating two targets tissues proximate to two respective non-target tissues is provided. The method includes monitoring a temperature difference between a first non-target tissue and a first nearby target tissue. An ultrasound focus is directed into the first target tissue (to heat the first target tissue) while a second non-target tissue (proximate to a second target tissue) is cooled. When the temperature difference between the first target tissue and the first non-target tissue exceeds a specified (e.g., clinically significant) threshold (e.g., 5° C.), the ultrasound focus is re-directed into the second target tissue (so as to heat it).

In yet another aspect, the invention is directed to an ultrasound treatment method including a plurality of treatment cycles. In each cycle, cooling of a non-target tissue is activated, ultrasound is focused into a target tissue proximate the non-target tissue so as to heat the target tissue, and cooling of the non-target tissue is deactivated. The cooling may be deactivated at a time when the target tissue is still being heated, or after heating of the target tissue has ceased. The temporal cycle of activating and deactivating may be established based on thermal properties of the target and non-target tissues. In some embodiments, the thermal time constant of the target tissue (i.e., the time scale on which the temperature of the target tissue changes in response to heating or cooling) is greater than the thermal time constant of the non-target tissue (or vice versa).

A further aspect of the invention relates to a controller or control facility for use in conjunction with a thermal treatment apparatus (such as, e.g., an ultrasound transducer) and temperature control equipment (such as, e.g., a cooling fluid circuit). The controller includes a module for processing monitored data indicative of a temperature field in a region encompassing the target tissue and a non-target tissue, and a module for controlling the temperature control equipment so as to adjust a temperature of the non-target tissue based (at least in part) on the monitored temperature field. The monitored data may include thermal imaging data supplied to the controller by an MRI or other imaging apparatus. Alternatively or additionally, the monitored data may include computed temperature data, and processing the data may involve computationally updating the temperature data in time. The controller may further include a module for driving the thermal treatment apparatus, either directly or via communication with a separate, dedicated driver of the thermal treatment apparatus.

In another aspect of the invention, a thermal treatment system is provided. The system includes a thermal treatment apparatus for heating a target tissue, temperature control equipment for adjusting a temperature of a non-target tissue, and a controller for driving the thermal treatment apparatus and/or controlling the temperature control equipment based, at least in part, on a monitored temperature field in a region encompassing the target tissue and the non-target tissue.

BRIEF DESCRIPTION OF THE DRAWINGS

The foregoing will be more readily understood from the following detailed description of the invention in conjunction with the drawings, wherein.

DETAILED DESCRIPTION

Figure 1:
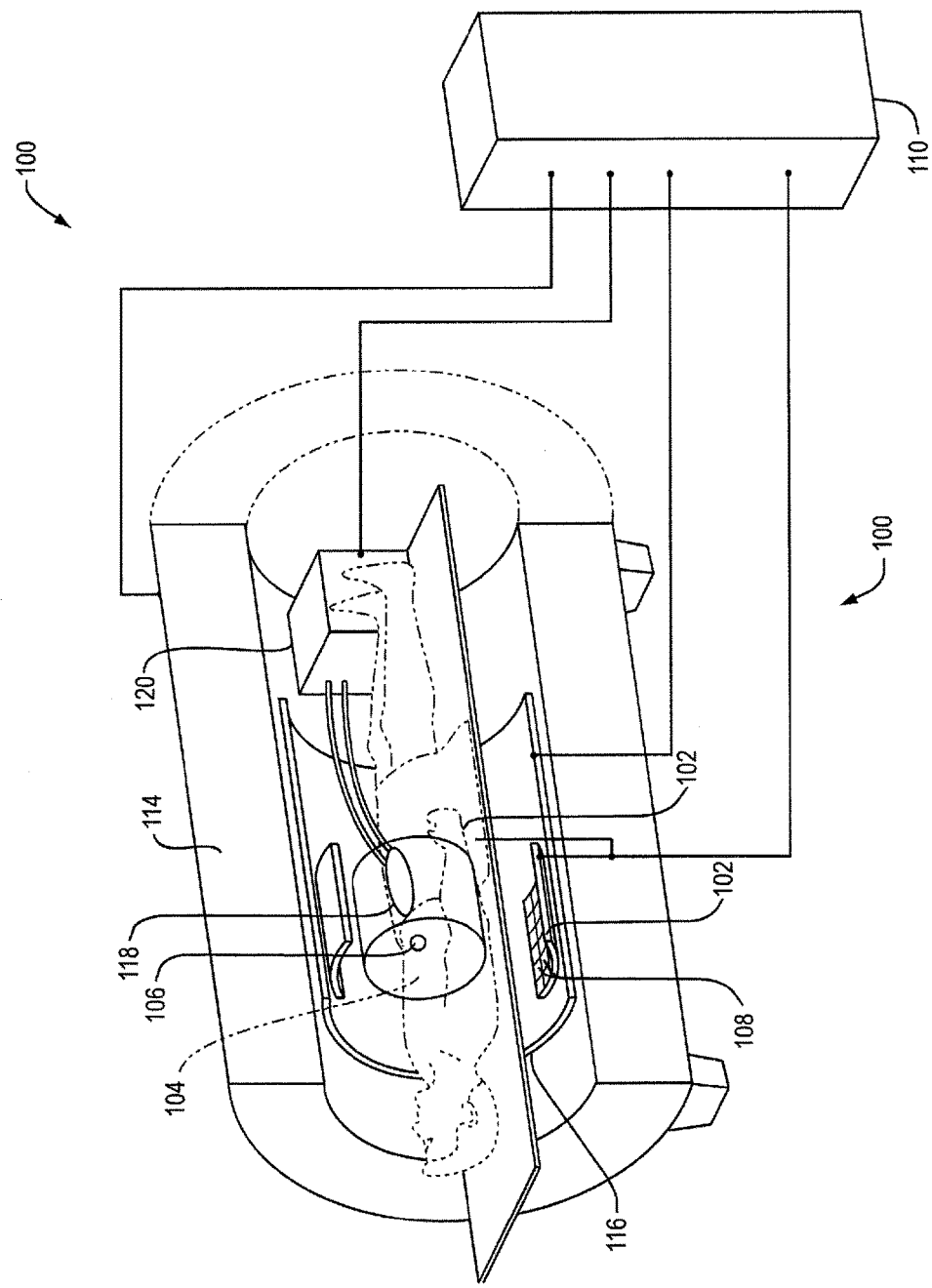
FIG. 1 is a schematic drawing illustrating a magnetic-resonance-guided focused ultrasound system (MRgFUS) for implementing treatment protocols in accordance with various embodiments.

The present invention generally relates to cooling protocols that are employed during medical treatment—in particular, thermal therapies—for the protection of non-target tissues. Thermal therapies, as the term is used herein, include any method that deliberately and selectively heats body tissues for the purpose of medical treatment. Typically, such methods aim at the destruction of unhealthy or tumorous tissues or at tissue removal during surgical procedures. However, thermal therapies also include palliative heat-treatment methods, and cooling protocols may find application in this area as well. Thermal treatment may be accomplished by heating a particular tissue or organ, or a portion thereof, with ultrasound, lasers, radio-frequency (RF) waves, or microwaves. In some of these techniques, heat is applied to a target tissue via convective or conductive propagation, and in others, waves (e.g., ultrasound) are directly focused into the target. During heat treatment of targeted tissue, non-targeted tissue may be affected inadvertently. Therefore, where the anatomy allows selective cooling of non-targeted tissue, active cooling may be used to improve treatment safety, i.e., to avoid damage to non-targeted tissue.

In various embodiments, the invention provides systems and methods for actively and dynamically manipulating the temperature of both a target tissue or organ to be treated, and its surrounding tissues and tissue interfaces. Compared with thermal treatment protocols that solely rely on passive cooling (i.e., waiting periods that interrupt thermal treatment to allow temperatures of non-target tissues to fall to safe levels), active cooling protocols may significantly reduce total treatment times. Further, dynamic temperature control addresses certain problems associated with fixed cooling temperatures. For example, dynamic cooling may involve regulating the cooling based on temperature feedback, thereby avoiding excessive cooling of non-target tissues without increasing the risk to non-target tissues.

Systems for use in accordance with the invention generally include a source of targeted thermal energy, and means for monitoring and/or actively manipulating the temperature in a relevant region of the patient's body. Thermal energy may be generated, for example, by absorption of ultrasound. A source of targeted thermal energy are, therefore, ultrasound transducers, which facilitate focusing ultrasound at a target such as, e.g., a tumor, and thereby heating the target. Other sources of thermal energy include RF or microwave generators and lasers. In some embodiments, cryoablation is utilized to destroy tissue by cycling between deep freezing and body temperature. Heat sources and cryoablation devices are collectively classified as tissue ablation device.

The temperature of the target and/or surrounding tissues may be monitored by a thermal imaging technique such as, e.g., thermal MRI. In some embodiments, it may be sufficient to monitor the skin surface temperature of the patient (e.g., using infrared cameras). As an alternative to imaging techniques, the temperature may be monitored (if necessary, invasively) by a collection of thermal sensors at various test locations. Further, in some embodiments, the temperature distribution in and around the target may be amenable to computational determination. Instead of measuring the temperature of the tissues over time, the temperature is then calculated based on anatomical dimensions and arrangements of tissues, known thermal tissue properties (such as, e.g., absorption and reflection coefficients, and heat capacity and thermal conductivity), and known parameters of thermal energy application to the target (e.g., total energy, intensity, and/or spatial distribution of the applied heat or heat-generating radiation; tissue absorption, perfusion, and/or diffusion parameters; and tissue thermal parameters). Computation of the time-evolution of the temperature field may involve computation calibrations, i.e., adjustments of parameters of the computations such that calculated temperature fields comport with accurately measured fields. Such calibrations may be desirable, for example, to adjust the computation to the tissue properties of a specific patient. The computation parameters generally relate the thermal state (e.g., the temperature distribution) of the tissues to the initial state and one or more thermal stimuli (such as applied or extracted energy); they characterize the thermal response of the tissues. In certain embodiments, some or all of the computation parameters are directly related to specific, well-defined physical tissue parameters, such as heat absorptivities or thermal time constants. However, this need not always be the case. The computation parameters may be or include parameters of a complex functional relationship between thermal stimuli and response that do not represent specific thermal properties, but the aggregate thermal response characteristics of the tissue.

Cooling (and, if desired, heating) of non-target tissues may be accomplished by bringing an accessible tissue interface (typically, the skin or a cavity that is accessible from outside the body) in contact with a heat sink (or source), preferably located in the vicinity of the tissue to be cooled (or heated). Such heat sinks may, for example, take the form of a balloon that will conform to the surface it is meant to cool, or a heat exchanger (typically, of a fixed shape) immersed in water that is in contact with the body surface. The rate of cooling may be controlled via the flow rate of coolant through the heat sinks, or via the temperature of the coolant. Heat sinks (or sources) may also be provided by solid heat-conducting components such as, e.g., bi-metal plates or stripes placed in contact with the skin and whose temperature may be controlled electronically.

FIG. 1 illustrates an exemplary system 100 adapted for use in thermal treatment methods that involve active cooling. The system 100 is a magnetic-resonance-guided focused ultrasound (MRgFUS) system. It includes an ultrasound transducer 102, which may be disposed near the torso 104 of a patient and directed towards a target 106 in a region of interest ("ROI") inside the patient. The transducer 102 may comprise a one- or two-dimensional array (i.e., a row or a matrix) of individually controllable transducer elements 108, or an irregular arrangement of transducer elements 108. The transducer 102 may have a curved (e.g., spherical or parabolic) shape, as illustrated, or may include one or more planar or otherwise shaped sections. Its dimensions may vary, depending on the application, between millimeters and tens of centimeters. The transducer elements 108 may be piezoelectric ceramic elements. Piezo-composite materials, or generally any materials capable of converting electrical energy to acoustic energy, may also be used.

The transducer elements 108 are separately controllable, i.e., they are each capable of emitting ultrasound waves at amplitudes and/or phases that are independent of the amplitudes and/or phases of the other transducer elements. Collectively, they form a "phased array" capable of steering the ultrasound beam in a desired direction, and moving it during a treatment session based on electronic control signals. The transducer elements 108 are driven by a control facility 110 in communication with the array. For n transducer elements 108, the control facility 110 may contain n control circuits, each comprising an amplifier and a phase delay circuit and driving one of the transducer elements. The control facility 110 may split a radio-frequency (RF) input signal, typically in the range from 0.1 MHz to 4 MHz, to provide n channels for the n control circuits. The control facility may be configured to drive the individual transducer elements 108 at the same frequency, but at different phases and different amplitudes so that they collectively produce a focused ultrasound beam. The control facility 110 may also include additional circuitry and switches that allow subsets of the transducer elements to be grouped into sub-arrays, and the elements within one sub-array to be driven at the same amplitude and phase.

The control facility 110 desirably provides computational functionality, which may be implemented in software, hardware, firmware, hardwiring, or any combination thereof, to compute the required phases and amplitudes for a desired focus location. For example, the control facility 110 may receive data indicative of the desired focus location (i.e., the target) relative to the ultrasound transducer, and account for the respective distances between each transducer element and the target, and the associated travel times of the acoustic waves that originate at the various transducer elements, in computing the phases. In general, the control facility may include several separable apparatus, such as a frequency generator, a beamformer containing the amplifier and phase delay circuitry, and a computer (e.g., a general-purpose computer) performing the computations and communicating the phases and amplitudes for the individual transducer elements 108 to the beamformer(s). Such systems are readily available or can be implemented without undue experimentation.

The system 100 further includes an MRI apparatus in communication with the control facility 110. The MRI apparatus facilitates monitoring the temperature of the target and surrounding tissues, which serves both to guide the ultrasound focus, and to provide feedback for active tissue cooling protocols. The apparatus includes a cylindrical electromagnet 114, which generates a static magnetic field within a bore thereof. During medical procedures, the patient may be placed inside the bore on a movable support table, and positioned such that an imaging region encompassing the ROI (e.g., a particular organ) falls within a region where the magnetic field is substantially uniform. The magnetic field strength within the uniform region is typically between about 1.5 and about 3.0 Tesla. The magnetic field causes hydrogen nuclei spins to align and precess about the general direction of the magnetic field. An RF transmitter coil 116 surrounding the imaging region emits RF pulses into the imaging region, causing some of the aligned spins to oscillate between a temporary high-energy non-aligned state and the aligned state. This oscillation induces RF response signals, called the magnetic-resonance (MR) echo or MR response signals, in a receiver coil, which may, but need not, be the transmitter coil 116. The MR response signals are amplified, conditioned, and digitized into raw data using an image processing system (which may be implemented, e.g., in control facility 110), and further transformed into a set of image data by methods known to those of ordinary skill in the art. Because the response signal is tissue- and temperature-dependent, a temperature map may be computed from the image data. Further, the target 106 (e.g., a tumor) may be identified in the image, and the ultrasound transducer 102 may then be driven so as to focus ultrasound into (or near) the treatment region.

The system 100 further includes temperature control equipment, such as, e.g., a pump circuit for pumping a cooling fluid (e.g., water) through a heat exchanger 118 in contact with the patient's skin. A pump module 120, which may also contain a heat exchanger and associated operating circuitry for setting the temperature of the cooling fluid, is connected to and operates pursuant to control signals from the control facility 110. The control facility 110 may include software and/or hardware modules that implement various treatment and cooling protocols. For example, the control facility 110 may continuously monitor the temperature of the target and surrounding tissues (using MRI thermometry), and drive both the transducer 102 and the pump module 120 based on the temperature data. Treatment and cooling protocols may specify sequences of sonication and cooling periods (which may or may not overlap in time), as well as sonication and cooling parameters (including, e.g., the location of the ultrasound focus, the energy and mode of the beam, and the temperature and flow rate of the cooling fluid), which may vary in time. Instead of or in addition to basing the control of the ultrasound transducer 102 and the pump circuit on thermal image data, the control facility 110 may also compute the thermal response of the irradiated and actively cooled tissues to heating and cooling according to the protocols from a-priori knowledge of the thermal properties of the affected tissues.

The exemplary thermal treatment system 100 may be straightforwardly modified in various ways. For example, the control functionality for driving the ultrasound transducer, monitoring the temperature field, and controlling the temperature control equipment need not be implemented in a single, integrated control facility 110. In some embodiments, the ultrasound transducer and its control and drive circuitry form a stand-alone thermal treatment apparatus, and the temperature control equipment (which facilitates cooling of non-target tissues) is controlled by a separate controller, which determines the temperature evolution, e.g., by computation or processing of thermal imaging data received from an MRI apparatus. The controller for the temperature control equipment may, but need not communicate with the ultrasound system controller.

The ability to monitor and adjust the temperature of non-target tissues during treatment improves the trade-off between treatment effectiveness, risk to non-target tissues, and treatment time. In general, to effectively treat a target tissue (e.g., to coagulate or ablate it), a certain treatment threshold, usually a temperature-time threshold, needs to be exceeded in the target tissue. (A temperature-time threshold typically means that the temperature in the target is at or above a certain value for a certain period of time.) Simultaneously, to avoid pain and damage to non-target tissue, the thermal condition of the non-target tissue needs to stay below a damage threshold, which is lower than the treatment threshold. If substantial uncertainties are associated with the temperatures of the target and non-target tissues because the temperature is neither measured nor accurately computed, the treatment protocol typically aims at a target temperature considerably above the treatment threshold to ensure effective thermal treatment of the target, and at a non-target temperature considerably below the damage threshold to provide a margin of safety. Due to the interdependence of target and non-target tissue temperatures, this increased temperature gap (compared with the temperature difference between the treatment and damage thresholds) may result in prolonged treatment durations. For example, the time needed to ablate a tumor may be increased by excessive cooling of surrounding non-target tissues. Accurate knowledge of the temperature field in a region encompassing both the target and the non-target tissues (in particular, those in the beam path zone), as provided in various embodiments of the present invention, facilitates heating the target to a temperature closer to the treatment threshold, and cooling the non-target tissue to a temperature closer to the damage threshold, which allows faster treatment without increasing risk of damage to non-targeted tissue.

Figure 2A:
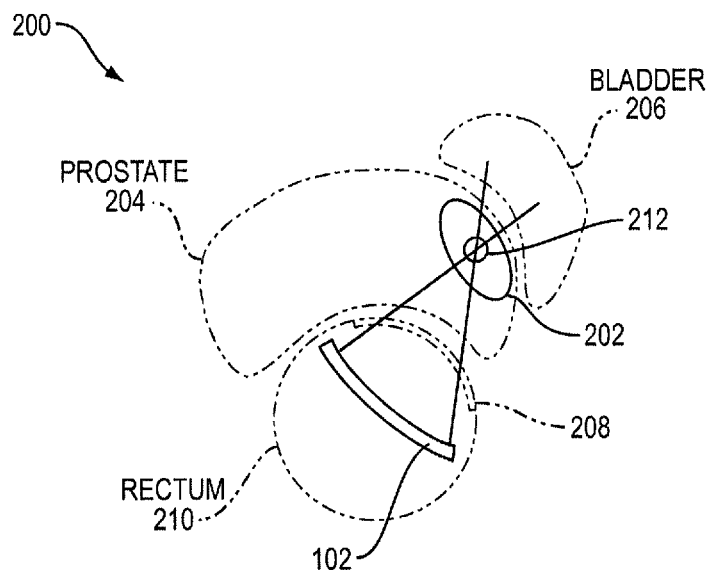
FIG. 2A is a schematic drawing illustrating an exemplary treatment scenario according to one embodiment in which the target is distant from a cooled tissue interface and proximate to a non-cooled non-target tissue.
Figure 2B:
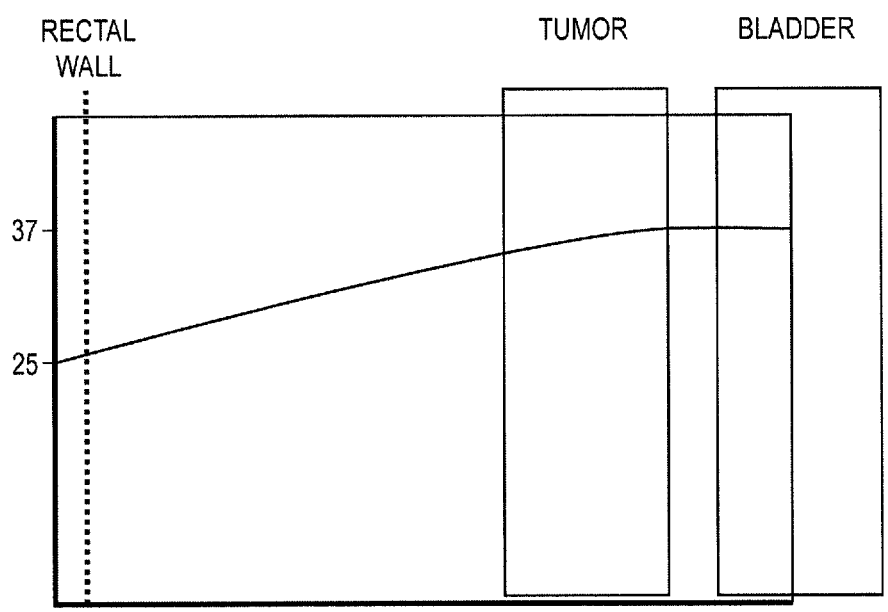
FIG. 2B is a graph illustrating the temperature profile of the treatment scenario shown in FIG. 2A.

Temperature monitoring and dynamic adjustment may be particularly useful if the trade-off involves multiple non-target tissues. An exemplary treatment scenario 200 is illustrated in FIG. 2A. In this scenario, a tumor 202 is located in an anterior region of the prostate 204, close to the bladder muscle 206. Ultrasound is applied through the rectal wall 208, and penetrates the posterior region of the prostate 204 before it reaches the tumor 202. Cooling the rectum 210 to protect the rectal wall 208 results in cooling of the whole prostate 204, including the tumor 202, but does not significantly affect the temperature of the bladder muscle 206 (i.e., the bladder muscle 206 remains substantially at body temperature). Accordingly, the cooling results in a temperature gradient between rectal wall 208, tumor 202, and bladder muscle 206, in which the target is at a lower temperature than the bladder muscle, as shown in FIG. 2B. This gradient implies a high risk for damage to the non-targeted bladder muscle 206 because the application of ultrasound at an energy level that suffices to effectively treat the tumor (despite the incidental active cooling of the tumor) also results in substantial heating of the bladder muscle 206. The energy needed for tumor treatment increases with the temperature gradient. Thus, by avoiding or reducing the cooling of the rectal wall 208, as may be possible if the temperature of the rectal wall 208 is continuously monitored, the risk to the bladder muscle 206 may be mitigated. The safety of the rectal wall 208 may be maintained at reduced cooling levels (i.e., at higher temperatures) because the beam passes the rectal wall at a significant distance from the focal zone 212, where its energy density is low.

Figure 3A:
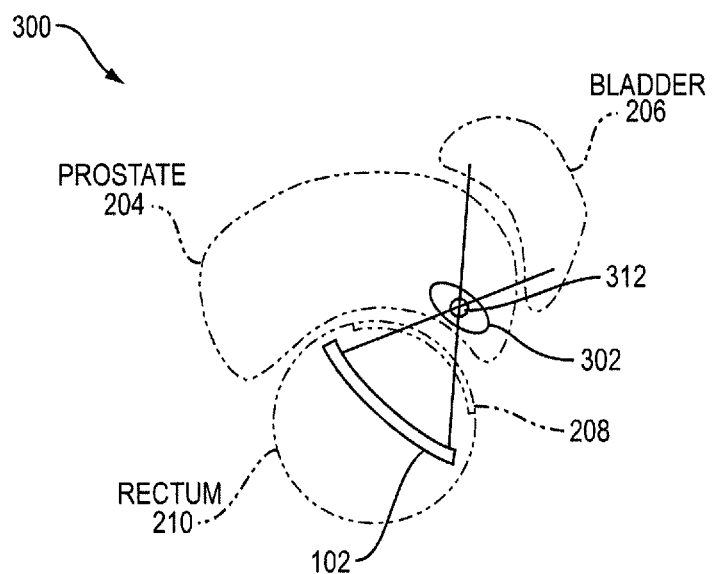
FIG. 3A is a schematic drawing illustrating an exemplary treatment scenario according to one embodiment in which the target is proximate to a cooled non-target tissue interface.
Figure 3B:
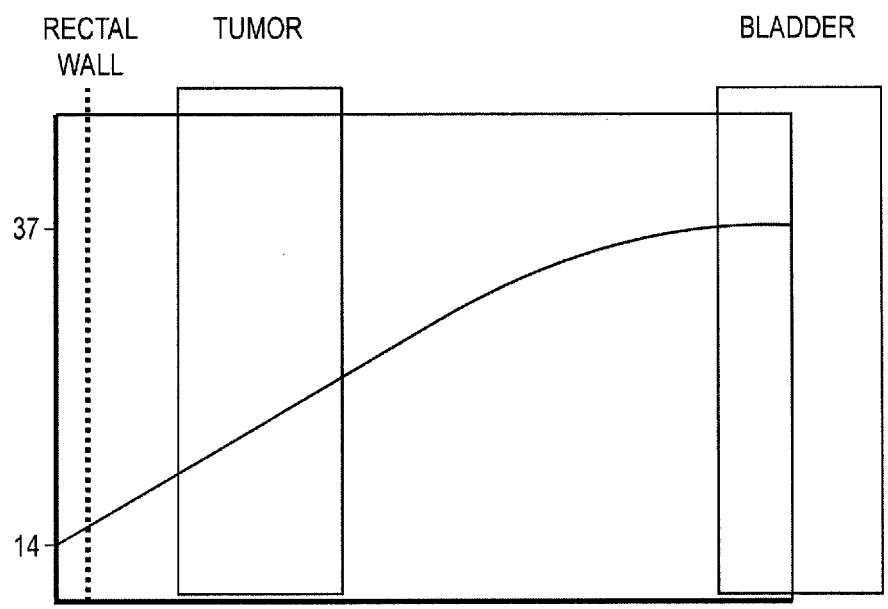
FIG. 3B is a graph illustrating the temperature profile of the treatment scenario shown in FIG. 3A.

FIG. 3A shows, by contrast, a treatment scenario 300 in which the tumor 302 is located in the peripheral zone of the prostate 204 close to the rectal wall 208. In this case, the ultrasound focus 312 is close to the rectal wall 208, and hence the energy density on the rectal wall 208 is high. To avoid damage to the rectal wall 208 that might result from heat accumulated during multiple sonications, in particular, if the acoustic absorption in the rectal wall 208 is higher than in the tumor 302, the rectal wall 208 may be actively cooled. FIG. 3B shows the thermal gradient profile resulting from cooling. As a comparison of FIGS. 3A and 3B reveals, the rectal wall 208 may be cooled down to significantly lower temperatures if the tumor 202 is close to the rectal wall 208 than if it is close to the bladder muscle 206. The temperature of the bladder muscle 206 is almost the same in both cases since it is barely influenced by the prostate temperature. When the rectal wall 208 near the prostate is actively cooled, the prostate temperature cools down in a non-uniform way (depending on the distance from the rectal wall, major blood vessels locations, diffusion and perfusion parameters, etc.). As a result, the prostate-tumor temperatures vary with the tumor location inside the prostate and the induced cooling temperature, as seen in FIGS. 2B and 3B.

Figure 4A:
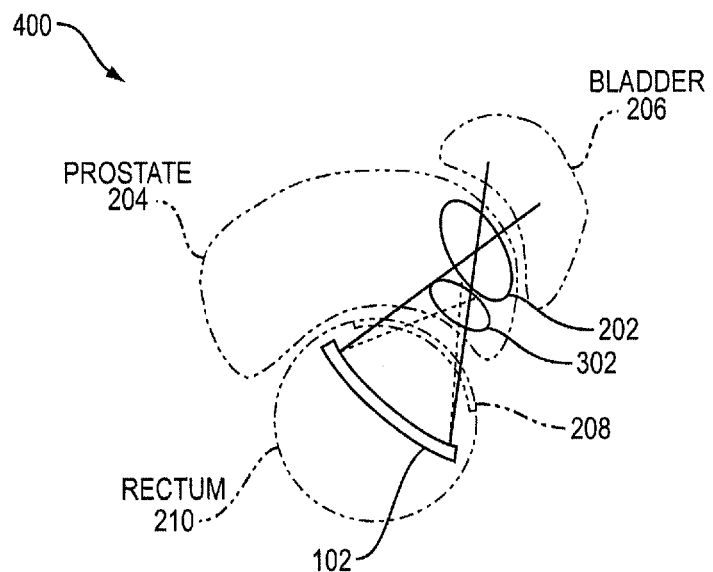
FIG. 4A is a schematic drawing illustrating an exemplary treatment scenario according to one embodiment which includes two targets proximate to a cooled tissue interface and a non-cooled non-target tissue, respectively.
Figure 4B:
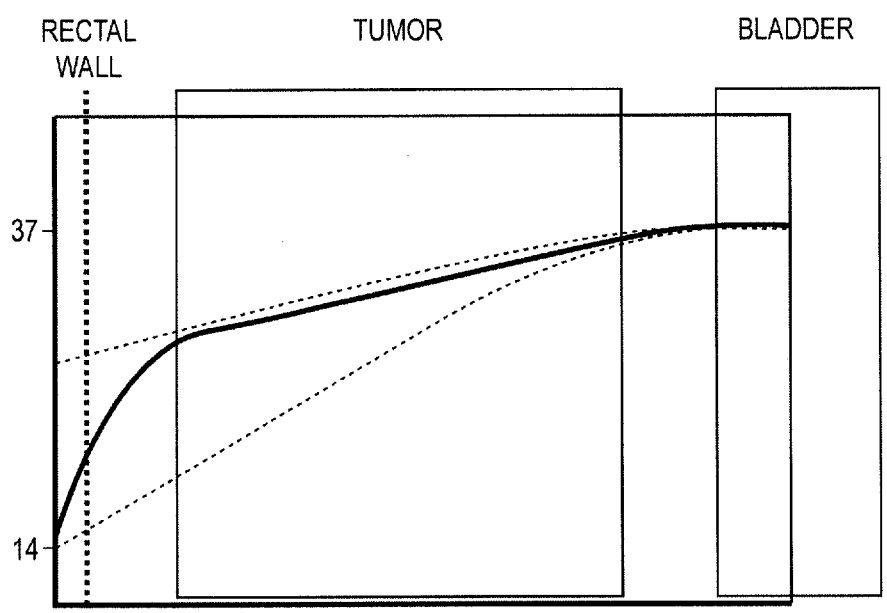
FIG. 4B is a graph illustrating the temperature profile of the treatment scenario shown in FIG. 4A.

FIG. 4A illustrates yet another treatment scenario 400, in which two tumors 202, 302 are present in the prostate 204, one close to the rectal wall 208 and one close to the bladder muscle 206. Effective treatment and cooling in this case can be accomplished by exploiting transient thermal states. More specifically, treatment may start with the sonication of the anterior tumor 202 close to the bladder muscle 206, and circulation of the chilled cooling liquid may begin. Sonication of the anterior tumor 202 continues as long as the temperature difference between the prostate 204 tissue surrounding the tumor region and the bladder muscle 206 does not exceed a certain threshold difference, for example, as long as the bladder muscle temperature is no more than 5° C. above the prostate temperature. Once this threshold is exceeded, the ultrasound focus is shifted to the posterior tumor 302. By that time, the rectal wall 208 has been sufficiently cooled to withstand the higher ultrasound intensity without damage, and the bladder muscle 206 is so far from the ultrasound focus that its temperature is not significantly affected by the acoustic beam that is now focused close to the rectal wall. FIG. 4B shows the transient temperature profile (not accounting for the increased tumor temperature due to sonication) between an initial profile at the onset of cooling, and a steady-state profile reached after an extended cooling period. The treatment sequence may be repeated if necessary to fully ablate both tumors 202, 302.

In some embodiments, treatment and cooling protocols take advantage of different thermal response characteristics of target and non-target tissues. For example, the target tissue may have a greater thermal time constant than the non-target tissue. The differences can originate from differences in anatomical position relative to the cooled surface, or from different tissue types (such as fat, muscle, etc.). The thermal time constant of a tissue is a metric of the speed with which the tissue reacts to cooling or heating by an external source of energy; specifically, it is the inverse of the rate of response. The temporal response of a tissue to externally induced cooling or heating depends, inter alia, on the specific tissue perfusion and diffusion properties and the relative fat/muscle content of the tissue. As a result, the tissue thermal time constant can vary between different tissues and organs. The time constant may be measured, for example, by exposing the tissue to an external source of heat or cooling, and measuring the time it takes for the specific tissue to reach 63% (1−1/e) of the induced temperature difference.

Figure 5:
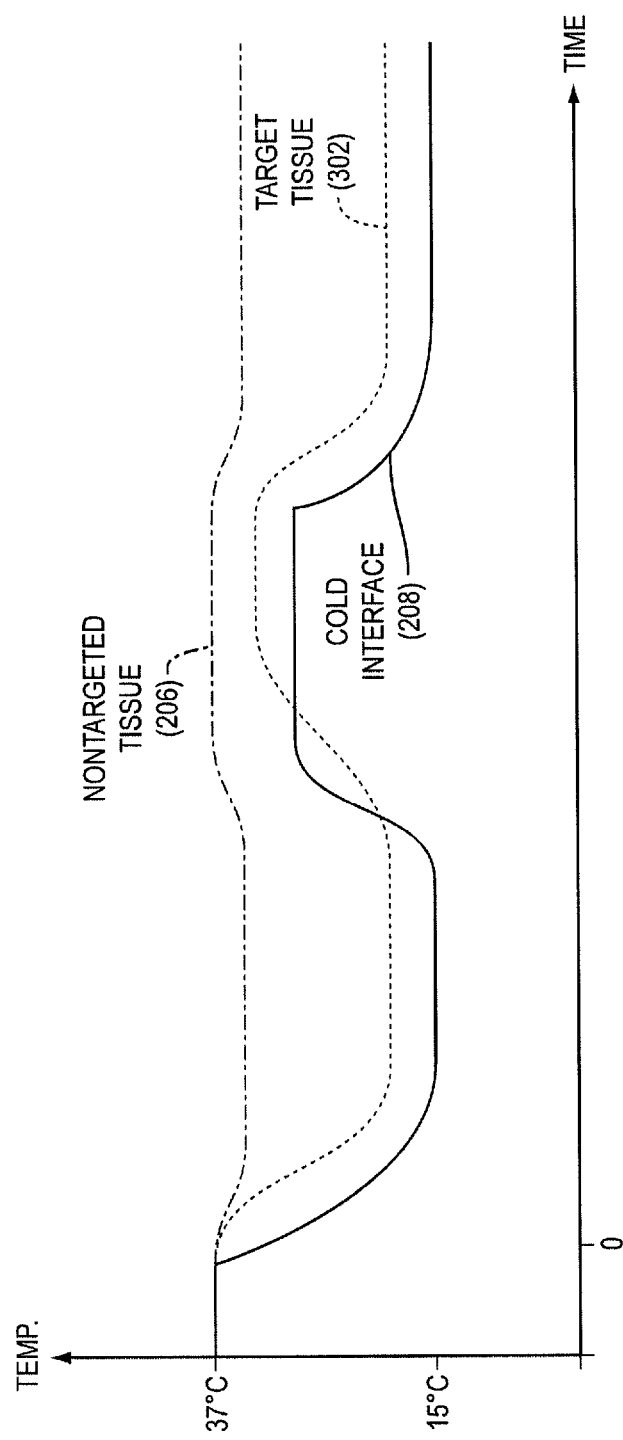
FIG. 5 is a graph illustrating the time development of the temperatures of target and non-target tissues in accordance with one embodiment.

Using disparate thermal time constants, it is possible to first cool the non-target tissue (thereby inadvertently cooling a nearby tumor, albeit at a lower rate), and then irradiate or otherwise heat the target. In some embodiments, cooling of the non-target tissue is deactivated during tumor treatment to avoid counter-acting the effect of heating the tumor. When the non-target tissue temperature approaches the damage threshold, tumor treatment is interrupted, and the non-target tissue is again cooled down. In alternative embodiments, cooling of the non-target tissue continues throughout the tumor treatment, and is deactivated thereafter. The non-target tissues may then be actively heated back up to the initial temperature (using, e.g., the fluid previously used for cooling, at a higher temperature). In either group of embodiments, the cycle of active cooling, target treatment, and deactivation of the cooling may be repeated multiple times. A dynamic treatment protocol that involves cycling of cooling and treatment may be used, for example, in the treatment scenario 300 illustrated in FIG. 3A. The rectal wall 208 generally cools down faster than a tumor 302, and, hence, dynamic cooling allows effective treatment of the tumor 302 at lower energy levels while protecting the rectal wall. FIG. 5 illustrates the time development of the temperatures at the rectal wall 208, the tumor 302, and the non-targeted bladder muscle 206.

Although the present invention has been described with reference to specific details, various modifications and combinations of described elements of various embodiments will be readily apparent to those of skill in the art, and are considered to be within the scope of the invention. For example, the (periodic) activation and deactivation of cooling may be combined with focus shifting between multiple targets or multiple regions within a larger target. Further, it is contemplated that different cooling regimes may be applied to different non-target tissues, using, e.g., two or more cooling circuits. Accordingly, it is not intended that any described details are regarded as limitations upon the scope of the invention, except as and to the extent that they are included in the accompanying claims.

What is claimed is:

1. A method for ultrasound treatment of two distinct target regions within a tissue, a first target region being proximate a first, non-coolable non-target tissue and a second target region being proximate a second, coolable non-target tissue, cooling of the second non-target tissue also causing cooling of the second target region and, to a lesser extent, cooling of the first target region, and heating of either target region also causing heating of at least a tissue region surrounding the respective target region and the non-target tissue proximate thereto, the method comprising:
   using an ultrasound transducer, directing an ultrasound focus first into the first target region so as to heat the first target region while cooling the second non-target tissue;
   using a thermal imaging device, monitoring a temperature of the first non-target tissue relative to a temperature of the tissue region surrounding the first target region; and
   when the temperature of the first non-target tissue exceeds the temperature of the tissue region surrounding the first target region by a specified threshold as a result of a combined effect of the ultrasound focus and the cooling, interrupting ultrasound treatment of the first target region so as to avoid overheating of the first non-target tissue and re-directing the ultrasound focus into the second target region so as to heat the second target region, whereby prior cooling of the second non-target tissue avoids overheating thereof.

2. The method of claim 1, wherein monitoring the temperature comprises magnetic resonance imaging thermometry.

3. The method of claim 1, wherein the temperature of the first non-target tissue is not affected to a clinically significant degree by heating of the second target region.

4. The method of claim 1, further comprising repeating all steps until a treatment objective is achieved.

5. A system for ultrasound treatment of two distinct target regions within a tissue, a first target region being proximate a first, non-coolable non-target tissue and a second target region being proximate a second, coolable non-target tissue, cooling of the second non-target tissue also causing cooling of the second target region and, to a lesser extent, cooling of the first target region, and heating of either target region also causing heating of at least a tissue region surrounding the respective target region and the non-target tissue proximate thereto, the system comprising:
   an ultrasound transducer for heating a target tissue;
   temperature control equipment for actively cooling the second non-target tissue but not the first non-target tissue; and
   a controller for driving the thermal treatment apparatus and controlling the temperature control equipment, based at least in part on a monitored temperature of the first non-target tissue relative to a temperature of the tissue region surrounding the first target region,
   wherein, when the first non-target tissue exceeds the temperature of the tissue region surrounding the first target region by a specified threshold as a result of a combined effect of the ultrasound focus and the cooling, the controller interrupts ultrasound treatment of the first target regions so as to avoid overheating of the first non-target tissue and re-directs the ultrasound focus into the second target region so as to heat the second target region, whereby prior cooling of the second non-target tissue avoids overheating thereof.

* * * * *